United States Patent
Shimuta et al.

(10) Patent No.: US 11,957,487 B2
(45) Date of Patent: Apr. 16, 2024

(54) COVER FOR ORAL DEVICE

(71) Applicant: Murata Manufacturing Co., Ltd., Nagaokakyo (JP)

(72) Inventors: Toru Shimuta, Nagaokakyo (JP); Kenji Tanaka, Nagaokakyo (JP); Jun Takagi, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 329 days.

(21) Appl. No.: 17/174,577

(22) Filed: Feb. 12, 2021

(65) Prior Publication Data

US 2021/0259630 A1    Aug. 26, 2021

(30) Foreign Application Priority Data

Feb. 26, 2020   (JP) ................................. 2020-030690
Sep. 30, 2020   (JP) ................................. 2020-165324

(51) Int. Cl.

| | |
|---|---|
| A61B 5/00 | (2006.01) |
| A61B 50/00 | (2016.01) |
| A61J 1/00 | (2023.01) |
| B32B 1/08 | (2006.01) |
| B32B 3/02 | (2006.01) |
| B32B 7/14 | (2006.01) |
| B32B 27/00 | (2006.01) |
| B32B 27/08 | (2006.01) |
| B32B 7/022 | (2019.01) |

(52) U.S. Cl.
CPC ............ *A61B 5/682* (2013.01); *A61B 5/4277* (2013.01); *A61B 5/6846* (2013.01); *A61B 50/00* (2016.02); *A61J 1/00* (2013.01); *B32B 1/08* (2013.01); *B32B 3/02* (2013.01); *B32B 7/14* (2013.01); *B32B 27/00* (2013.01); *B32B 27/08* (2013.01); *A61B 2050/002* (2016.02); *A61B 2562/16* (2013.01); *A61B 2562/247* (2013.01); *B32B 7/022* (2019.01); *B32B 2307/546* (2013.01); *Y10T 428/1334* (2015.01); *Y10T 428/1352* (2015.01)

(58) Field of Classification Search
CPC ..... A61B 5/682; A61B 5/4277; A61B 5/6846; A61B 50/00; A61B 2050/002; A61B 2562/16; A61B 2562/247; A61B 2562/029; A61B 5/4261; A61B 5/05; A61B 2562/164; A61J 1/00; B32B 1/08; B32B 27/00; B32B 7/022; B32B 2307/546; Y10T 428/1334; Y10T 428/1352

See application file for complete search history.

(56) References Cited

FOREIGN PATENT DOCUMENTS

| | | |
|---|---|---|
| JP | 2013195118 A | 9/2013 |
| WO | 2004028359 A1 | 4/2004 |

*Primary Examiner* — James C Yager
(74) *Attorney, Agent, or Firm* — Arentfox Schiff LLP

(57) ABSTRACT

A cover for covering an oral device that includes a first sheet member made of a first resin, and a second sheet member made of a second resin and facing the first sheet member, wherein when a first direction is a direction along a surface of the first sheet member and a second direction is a direction along the surface of the first sheet member and orthogonal to the first direction, the first sheet member and the second sheet member are joined to each other in a bag shape so as to define an opening at a first side in the first direction. A protruding portion protrudes from the second sheet member and past an outer edge of the first sheet member at the opening in the first direction.

17 Claims, 6 Drawing Sheets

COVER FOR ORAL DEVICE

CROSS REFERENCE TO RELATED APPLICATIONS

The present application claims priority to Japanese Patent Application No. 2020-030690, filed Feb. 26, 2020, and Japanese Patent Application No. 2020-165324, filed Sep. 30, 2020, the entire contents of each of which are incorporated herein by reference.

BACKGROUND OF THE INVENTION

Field of the Invention

The present disclosure relates to a cover for an oral device that is used in the mouth.

Description of the Related Art

International Publication No. 2004/028359 (hereinafter referred to as Patent Document 1) describes an oral device that is used in the mouth. The oral device is rod-shaped overall. This type of oral device is covered with a cover when used so that a portion of the oral device that is inserted into the mouth does not come into direct contact with the mouth.

The cover described in Patent Document 1 includes a pair of rectangular sheets arranged to face each other and bonded together at three sides thereof to form a bag shape with an opening. The cover is attached to the oral device by inserting the oral device into the opening of the cover.

When the oral device is being inserted into the cover described in Patent Document 1, there is a possibility that the cover will not open smoothly and the oral device cannot be easily inserted. When the cover cannot be easily attached to the oral device, the cover may, for example, become wrinkled while being attached to the oral device. If a sensor portion of the oral device is covered with a wrinkled portion of the cover, there is a risk that accurate measurement cannot be performed.

SUMMARY OF THE INVENTION

To solve the above-described problem, according to preferred embodiments of the present disclosure, a cover for covering at least a portion of an oral device that is used in a mouth includes a first sheet member made of a first resin, and a second sheet member made of a second resin and disposed to face the first sheet member. When a first direction is a direction along a surface of the first sheet member and a second direction is a direction along the surface of the first sheet member and orthogonal to the first direction, the first sheet member and the second sheet member are joined to each other in a bag shape so as to define an opening at a first side in the first direction. A protruding portion protrudes from the second sheet member and past an outer edge of the first sheet member at the opening in the first direction.

According to the above-described structure, the cover includes the two sheet members that form a bag shape with an opening. The second sheet member includes the protruding portion at the opening, and that is longer than the first sheet member. Accordingly, the cover can be easily opened by raising the protruding portion of the second sheet member, so that the oral device can be easily inserted into the cover.

According to the preferred embodiments of the present disclosure, the occurrence of wrinkles can be reduced.

Other features, elements, characteristics and advantages of the present invention will become more apparent from the following detailed description of preferred embodiments of the present invention with reference to the attached drawings.

DETAILED DESCRIPTION OF THE PREFERRED EMBODIMENTS

A cover according to a first embodiment will now be described. The cover is for an oral device that is used in the mouth. First, the oral device to be covered with the cover according to the present embodiment will be described.

Figure 1:
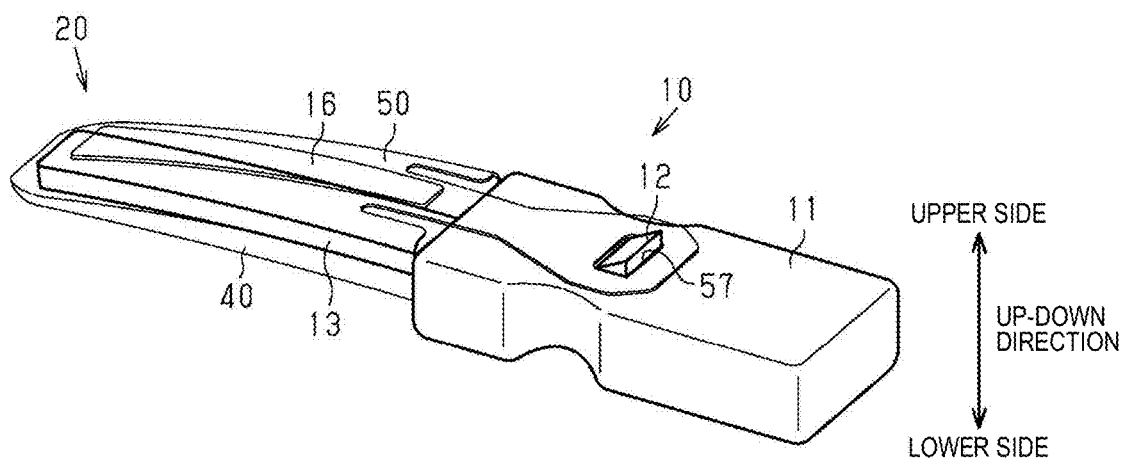
FIG. 1 is a perspective view of a cover according to a first embodiment that is attached to an oral device.

Referring to FIG. 1, an oral device 10 is a moisture measurement device that measures the amount of moisture in the mouth. The oral device 10 is substantially rod-shaped overall. Substantially half of the oral device 10 at one side in a longitudinal direction constitutes a grip portion 11 to be gripped by a user. The grip portion 11 is substantially rectangular-parallelepiped-shaped. Among the four surfaces of the grip portion 11 that extend in the longitudinal direction, an upper surface has a projecting portion 12 that projects therefrom. The projecting portion 12 is substantially triangular-prism-shaped, and extends in a width direction of the grip portion 11. One of the three rectangular side surfaces of the triangular prism is in contact with the upper surface of the grip portion 11. In the following description, the direction in which the projecting portion 12 protrudes is defined as an up-down direction. The side toward which the projecting portion 12 protrudes is defined as an upper side, and the side opposite thereto is defined as a lower side.

An extending portion 13 extends overall in the longitudinal direction from an end surface of the grip portion 11 at the other side in the longitudinal direction. The extending portion 13 is substantially flat-prism-shaped. The extending portion 13 is thinner than the grip portion 11. The extending portion 13 is gently curved downward toward the distal end of the extending portion 13.

Figure 2:
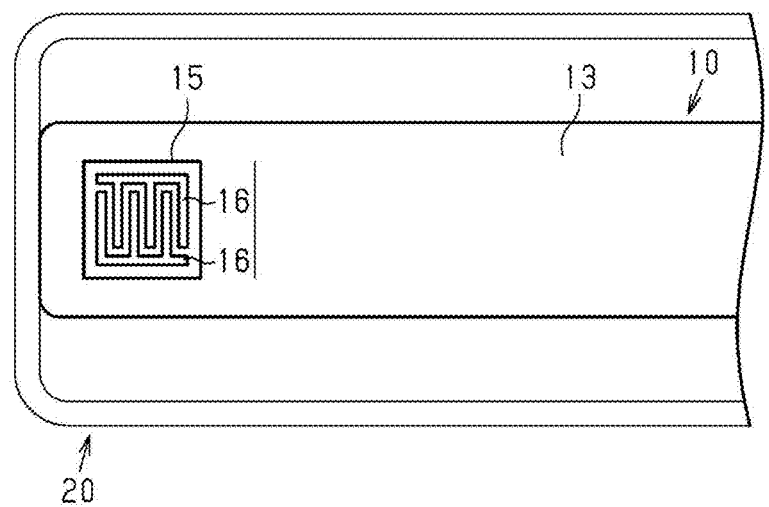
FIG. 2 is an enlarged view of a measurement portion and a portion of the cover according to the first embodiment.

As illustrated in FIG. 2, a sensor 15 is attached to a lower surface of a distal end portion of the extending portion 13. In the present embodiment, the sensor 15 is an electrostatic capacity type sensor. The sensor 15 includes a pair of electrodes 16. The pair of electrodes 16 are arranged in an interdigitated pattern. The pair of electrodes 16 function as electrodes of a capacitor. In other words, a measurement object that faces the sensor 15 and liquid on a surface of the measurement object function as a dielectric between the pair of electrodes 16. The capacitance between the pair of electrodes 16 corresponds to the amount of moisture inside and on the surface of the measurement object.

Although not illustrated, a circuit board on which components including an oscillation circuit and a control circuit are installed is mounted in the oral device 10. The oscillation circuit outputs a signal with a frequency corresponding to the capacitance of the sensor. The control circuit detects the amount of moisture in and on the measurement object based on the number of pulses of the signal output from the oscillation circuit. The control device displays the detected amount of moisture on a display (not shown).

The structure of a cover 20 for the above-described oral device 10 will now be described. The cover 20 is used to cover the extending portion 13 of the oral device 10.

Figure 3:
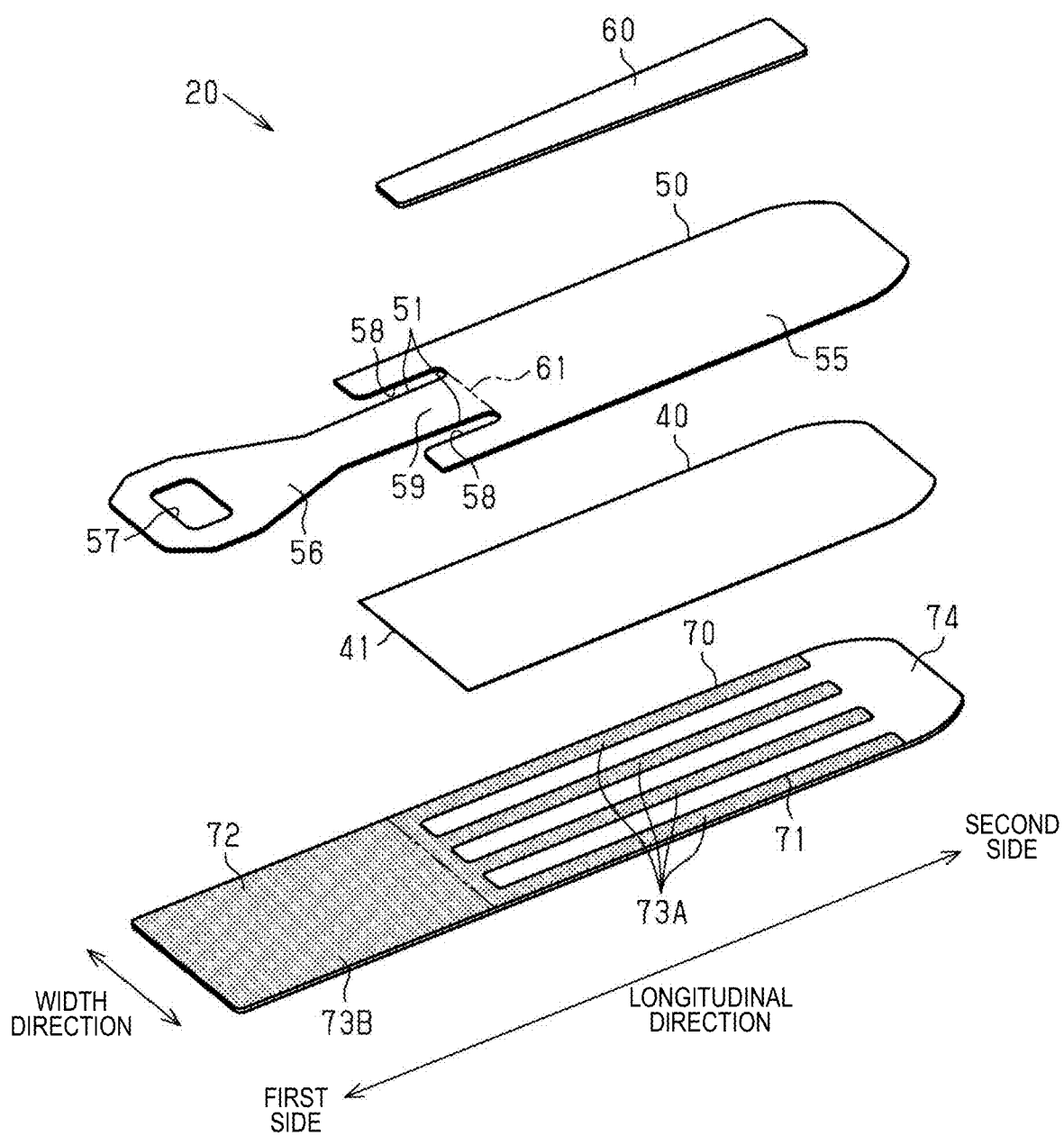
FIG. 3 is an exploded perspective view of the cover according to the first embodiment.

As illustrated in FIG. 3, the cover 20 includes a first sheet member 40 that is substantially rectangular. In the following description, the direction in which long sides of the first sheet member 40 extend is defined as a longitudinal direction, which corresponds to a first direction, and the direction in which short sides of the first sheet member 40 extend is defined as a width direction, which corresponds to a second direction.

An outer edge 41 of the first sheet member 40 at a first side in the longitudinal direction preferably extends straight along the width direction. Both corners of the first sheet member 40 at the first side in the longitudinal direction are preferably right-angle corners. Both corners of the first sheet member 40 at a second side in the longitudinal direction are preferably rounded. The material of the first sheet member 40 is a synthetic resin, and may be, for example, a polyethylene terephthalate (PET). The thickness of the first sheet member 40 is preferably about 10 micrometers to about 20 micrometers.

A second sheet member 50 is disposed to face the first sheet member 40 at one side of the first sheet member 40 in the thickness direction.

Figure 4:
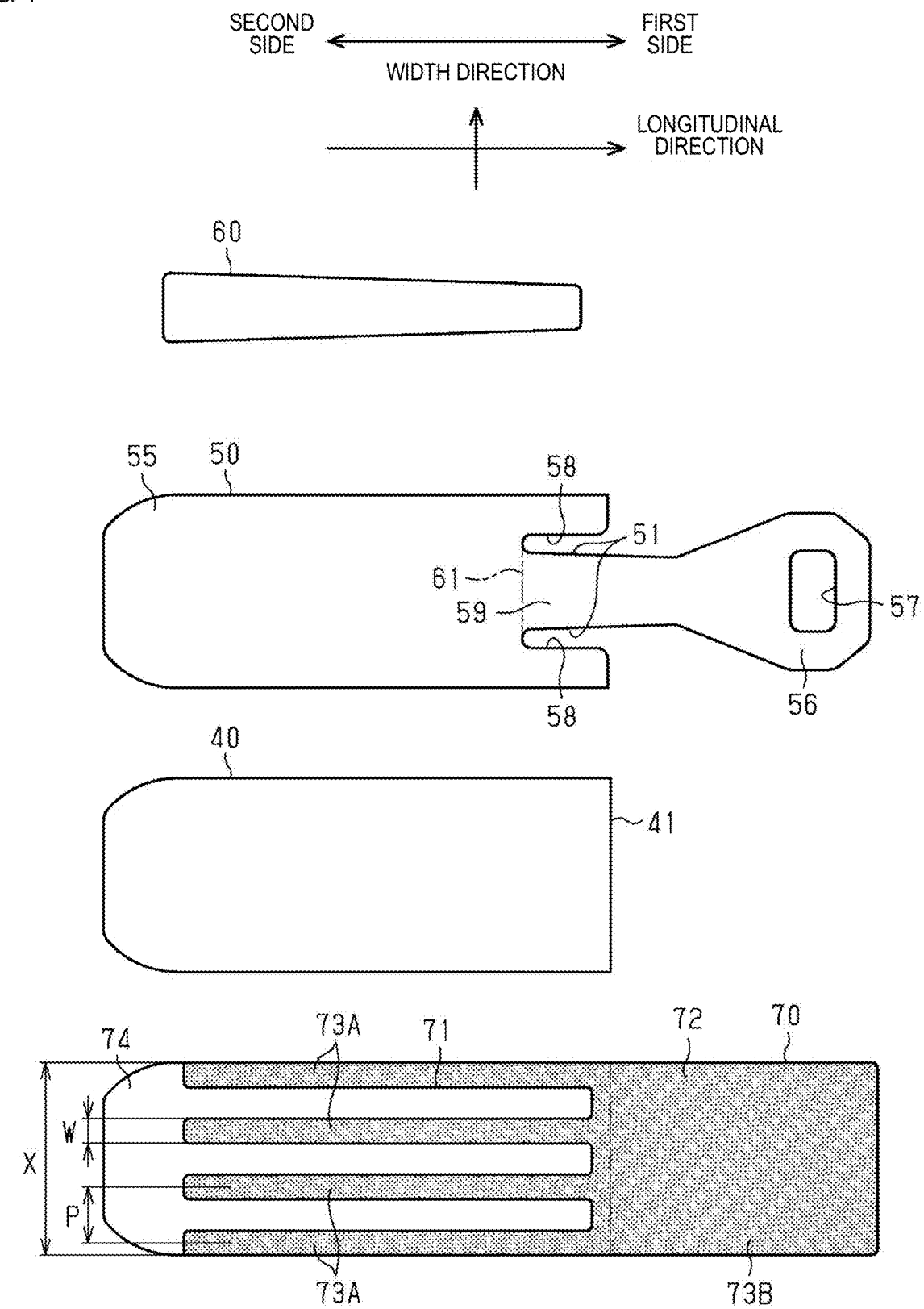
FIG. 4 is an exploded plan view of the cover according to the first embodiment.

As illustrated in FIG. 4, the second sheet member 50 includes a main portion 55 that overlaps the first sheet member 40. The main portion 55 is substantially rectangular. The length of the main portion 55 in the longitudinal direction is preferably equal to the length of the first sheet member 40 in the longitudinal direction. The length of the main portion 55 in the width direction is preferably equal to the length of the first sheet member 40 in the width direction. Both corners of the main portion 55 at the second side in the longitudinal direction are preferably rounded similarly to the corners of the first sheet member 40. Namely, the shape of the main portion 55 is substantially the same as that of the first sheet member 40.

The main portion 55 of the second sheet member 50 is stacked on the first sheet member 40 such that the contour of the main portion 55 coincides with the contour of the first sheet member 40. The main portion 55 of the second sheet member 50 and the first sheet member 40 are joined together at the edges thereof at the second side in the longitudinal direction and both sides in the width direction. Thus, the second sheet member 50 and the first sheet member 40 are joined together to form a substantially bag-like shape that can be opened at the first side of the sheet members in the longitudinal direction.

The main portion 55 has two slits 58 that extend from the outer edge 41 of the first sheet member 40 at the first side in the longitudinal direction toward the second side in the longitudinal direction. The two slits 58 are disposed one on each side of the center of the main portion 55 in the width direction. The two slits 58 extend parallel to each other by the same length.

The main portion 55 includes a lift-up portion 59 in a region between the two slits 58. The entirety of the lift-up portion 59 including both edges 51 of the lift-up portion 59 in the width direction is not joined to the first sheet member 40.

A protruding portion 56 protrudes toward the first side in the longitudinal direction from the outer edge of the main portion 55 at the first side in the longitudinal direction. In other words, the protruding portion 56 protrudes outward so as to protrude past the outer edge 41 of the first sheet member 40.

The edge of the protruding portion 56 at the second side in the longitudinal direction is continuously connected to the edge of the lift-up portion 59 at the first side in the longitudinal direction. Thus, the protruding portion 56 and the lift-up portion 59 adjoin each other. The length of the protruding portion 56 in the width direction at the second side in the longitudinal direction is equal to the length of the lift-up portion 59 in the width direction at the first side in the longitudinal direction. More specifically, the two slits 58 are arranged one on each side of the protruding portion 56 in the width direction, and the length of the protruding portion 56 in the width direction at the second side in the longitudinal direction is the length between the two slits 58. The overall shape of the protruding portion 56 is such that the length thereof in the width direction gradually increases from the second side toward the first side in the longitudinal direction. A wide portion of the protruding portion 56 at the first side in the longitudinal direction has a substantially rectangular through hole 57 that extends therethrough.

The material of the second sheet member 50 is a synthetic resin, and may be, for example, a polyethylene terephthalate (PET). In the present embodiment, the first sheet member 40 and the second sheet member 50 are made of the same PET. The thickness of the second sheet member 50 is preferably about 40 micrometers to about 60 micrometers. The overall body of the second sheet member 50 including the main portion 55 and the protruding portion 56 has a flexural rigidity higher than that of the first sheet member 40. The flexural rigidities of the sheet members are measured by the measurement method according to JIS K 7171:2016. This also applies to the following description regarding flexural rigidity.

A substantially sheet-shaped support member 60 is joined to the second sheet member 50 at a side opposite to the side at which the first sheet member 40 is provided. The support member 60 is substantially trapezoid-shaped and has a pair of bases at the first side and the second side in the longitudinal direction. The overall shape of the support member 60 is such that the length thereof in the longitudinal direction is greater than the length thereof in the width direction. The base of the support member 60 at the first side is shorter than the base of the support member 60 at the second side. The length of the base of the support member 60 at the first side in the longitudinal direction is less than the length of a boundary edge 61 of the lift-up portion 59.

As illustrated in FIG. 3, the support member 60 is disposed to extend across the boundary edge 61 of the lift-up portion 59 of the second sheet member 50 at the second side in the longitudinal direction. The boundary edge 61 of the lift-up portion 59 is a line connecting the ends of the two slits 58.

The material of the support member 60 is a synthetic resin, and may be, for example, a PET. The thickness of the support member 60 is preferably about 70 micrometers to about 80 micrometers. The flexural rigidity of the support member 60 is higher than the flexural rigidity of the second sheet member 50.

As illustrated in FIG. 4, a protective sheet 70 is joined to the first sheet member 40 at a side opposite to the side at which the second sheet member 50 is provided. The length of the protective sheet 70 in the longitudinal direction is slightly greater than the length of the second sheet member 50 in the longitudinal direction. The length of the protective sheet 70 in the width direction is substantially equal to the length of the first sheet member 40 and the main portion 55 of the second sheet member 50 in the width direction. The protective sheet 70 has a facing surface 71 that faces the first sheet member 40 and whose contour is the same as that of the first sheet member 40. Accordingly, both corners of the protective sheet 70 at the first side in the longitudinal direction are rounded similarly to the corners of the first sheet member 40.

The protective sheet 70 has the facing surface 71 and a non-facing surface 72. When the protective sheet 70 is joined to the first sheet member 40, the facing surface 71 faces the first sheet member 40, and the non-facing surface 72 does not face the first sheet member 40. The facing surface 71 of the protective sheet 70 includes an adhesive portion 74 that is adhesive to another sheet member and non-adhesive portions 73A that are not adhesive to another sheet member. The non-facing surface 72 of the protective sheet 70 preferably includes only a non-adhesive portion 73B that is not adhesive to another sheet member. The adhesiveness of the adhesive portion 74 with respect to another sheet member is such that the protective sheet 70 can be peeled by the hand or fingers without, for example, tearing the sheet member. Thus, the protective sheet 70 is removably joined to the first sheet member 40.

The facing surface 71 of the protective sheet 70 includes four non-adhesive portions 73A that are substantially rectangular and that extend in the longitudinal direction. The edges of the four non-adhesive portions 73A at the second side in the longitudinal direction do not reach the outer edge of the facing surface 71 at the second side in the longitudinal direction. As a result, the adhesive portion 74 extends along an end portion of the facing surface 71 at the second side in the longitudinal direction over the entire length of the facing surface 71 in the width direction.

Among the four non-adhesive portions 73A, two non-adhesive portions 73A at both ends in the width direction are disposed at the edges of the facing surface 71 in the width direction. These two non-adhesive portions 73A may instead be disposed near, not on, the ends of the facing surface 71 in the width direction. The four non-adhesive portions 73A are arranged at equal intervals in the width direction of the facing surface 71. A pitch P of the non-adhesive portions 73A in the width direction of the facing surface 71 is determined in advance so that the pitch P is not an integer ratio of a length X of the facing surface 71 in the width direction at the first side. A maximum length W of the substantially rectangular non-adhesive portions 73A in the width direction is greater than or equal to about 10% of the length X of the facing surface 71 in the width direction at the first side. In the present embodiment, the maximum length W of the non-adhesive portions 73A in the width direction is about 15% of the length X of the facing surface 71 in the width direction at the first side.

The material of the protective sheet 70 is a synthetic resin, and may be, for example, a polyethylene terephthalate (PET). In the present embodiment, the protective sheet 70 is made of the same PET as that of, for example, the first sheet member 40. The thickness of the protective sheet 70 is preferably about 70 micrometers to about 80 micrometers. The overall body of the protective sheet 70 has a flexural rigidity higher than that of the second sheet member 50.

The operation of the first embodiment will now be described.

To attach the cover 20 to the oral device 10, first, the cover 20 is positioned such that the protective sheet 70 is at the lower side. In this state, the user holds the protruding portion 56 of the second sheet member 50 and raises the protruding portion 56 upward. As the protruding portion 56 is raised, the lift-up portion 59 of the second sheet member 50 is also raised upward. When the lift-up portion 59 is raised upward, a portion of the first sheet member 40 that has been positioned under the lift-up portion 59 appears.

In addition, when the lift-up portion 59 is raised upward, the entire body of the second sheet member 50 is also raised upward. At this time, the first sheet member 40 may be urged to move upward together with the second sheet member 50 stacked thereon. However, the first sheet member 40 is pulled downward due to the adhesiveness of the protective sheet 70 disposed below the first sheet member 40. As a result, even when the second sheet member 50 is raised upward, the first sheet member 40 is not raised upward. Thus, the first sheet member 40 and the second sheet member 50 open to create a space therebetween.

Both end portions of the first sheet member 40 in the width direction are joined to the second sheet member 50, and the non-adhesive portions 73A are disposed at both end portions of the protective sheet 70 in the width direction. Therefore, when the second sheet member 50 is raised, the end portions of the first sheet member 40 in the width direction are raised together with the second sheet member 50. As a result, the first sheet member 40 and the second sheet member 50 open.

Next, the oral device 10 is positioned such that the sensor 15 faces downward, and is inserted into the space created between the first sheet member 40 and the second sheet member 50. At this time, the oral device 10 is inserted with the sensor 15 placed on the first sheet member 40 exposed when the lift-up portion 59 is raised. When the oral device 10 is inserted in this manner, the oral device 10 can be reliably inserted into the space between the first sheet member 40 and the second sheet member 50 and prevented from being inserted into a different space by mistake.

The oral device 10 is inserted until the distal end of the oral device 10 reaches the end of the first sheet member 40 and the second sheet member 50 at the second side in the longitudinal direction. When the oral device 10 is inserted in this manner, the shape of the space between the first sheet member 40 and the second sheet member 50 changes to a substantially columnar shape that corresponds to the shape of the oral device 10.

After the oral device 10 is inserted into the cover 20, the projecting portion 12 of the oral device 10 is engaged with the through hole 57 in the second sheet member 50, as illustrated in FIG. 1. Thus, the cover 20 is restrained from moving relative to the oral device 10 in a direction toward the distal end of the oral device 10. After that, the protective sheet 70 is removed from the first sheet member 40 by raising the oral device 10 upward together with the first sheet member 40, the second sheet member 50, and the support member 60 while holding the protective sheet 70. As a result, only the first sheet member 40 is disposed to face the sensor 15 of the oral device 10, so that the measurement in the mouth can be performed by the sensor 15.

The effects of the first embodiment will now be described.

(1-1) In the present embodiment, the second sheet member 50 includes the protruding portion 56 that protrudes from the outer edge 41 of the first sheet member 40 toward an outer side of the first sheet member 40 in the longitudinal direction. By holding the protruding portion 56 and raising the protruding portion 56 upward, the second sheet member 50 can be easily moved away from the first sheet member 40, so that the cover 20 including the two sheet members can be easily opened to create a space therein. As a result, the oral device 10 can be easily inserted into the space, and the cover 20 can be easily attached to the oral device 10.

(1-2) To prevent reduction in the measurement sensitivity of the sensor 15 of the oral device 10 according to the present embodiment, the first sheet member 40 that covers the sensor 15 of the oral device 10 is preferably thin. According to the present embodiment, the first sheet member 40 has a thickness of about 10 micrometers to about 20 micrometers, and is sufficiently thinner than other sheet members of the cover 20. Therefore, the sensitivity of the sensor 15 of the oral device 10 can be easily maintained at an appropriate level.

(1-3) In the present embodiment, the second sheet member 50 has a relatively high flexural rigidity. When an appropriately rigid sheet is used as the second sheet member 50 as in this case, the second sheet member 50 can be easily held by, for example, the hand or fingers. In addition, since the second sheet member 50 has a relatively high flexural rigidity, the second sheet member 50 does not easily buckle when the protruding portion 56 is raised. Accordingly, the first sheet member 40 and the second sheet member 50 easily open to create a space that extends in the longitudinal direction therebetween. Therefore, the oral device 10 can be easily inserted into the space that extends in the longitudinal direction.

(1-4) In the present embodiment, the main portion 55 of the second sheet member 50 includes the lift-up portion 59. When the lift-up portion 59 is raised upward to insert the oral device 10, a portion of the first sheet member 40 that does not overlap the second sheet member 50 appears on the surface. By sliding the oral device 10 along this portion, the cover 20 can be easily attached to the oral device 10.

(1-5) In the present embodiment, the substantially sheet-shaped support member 60 is joined to the second sheet member 50 at a side opposite to the side at which the first sheet member 40 is provided. The support member 60 has a flexural rigidity higher than that of the second sheet member 50. Therefore, when the protruding portion 56 of the second sheet member 50 is raised upward, a portion of the second sheet member 50 to which the support member 60 is joined can be easily raised upward without buckling. When the second sheet member 50 is raised upward over the entire region in which the support member 60 is joined thereto, the hollow space between the first sheet member 40 and the second sheet member 50 easily expands in the longitudinal direction, thereby facilitating the insertion of the oral device 10.

(1-6) When the protruding portion 56 of the second sheet member 50 is raised upward, there is a risk that the second sheet member 50 will buckle at the boundary edge 61 of the lift-up portion 59 at the second side. If the second sheet member 50 buckles at the boundary edge 61, there is a risk that only the protruding portion 56 of the second sheet member 50 will be raised and the main portion 55 cannot be moved away from the first sheet member 40. In the present embodiment, the support member 60 is disposed to extend across the boundary edge 61 in the longitudinal direction. Therefore, the risk of buckling of the second sheet member 50 at the boundary edge 61 can be reduced.

(1-7) In the present embodiment, the slits 58 are formed so that the length of the protruding portion 56 in the width direction at the second side in the longitudinal direction of the second sheet member 50 is less than the length of the second sheet member 50 along the outer edge 41 of the first sheet member 40. When the protruding portion 56 has a short length in the width direction at the second side thereof in the longitudinal direction of the second sheet member 50, the protruding portion 56 can be easily raised mainly at and around the second side thereof in the longitudinal direction. In the present embodiment, the protruding portion 56 is disposed in a central region of the second sheet member 50 in the width direction. Since the first sheet member 40 and the second sheet member 50 open mainly in the central region of the second sheet member 50 in the width direction, the hollow space therebetween easily expands in the first direction.

(1-8) In the present embodiment, the protective sheet 70 is removably joined to the first sheet member 40. The protective sheet 70 is removed from the first sheet member 40 when the measurement is performed. Namely, the first sheet member 40 can be protected by the protective sheet 70 until the measurement is performed, so that dust and the like do not easily adhere to the first sheet member 40 and that the first sheet member 40 can be maintained in a sanitary condition.

(1-9) In the present embodiment, the facing surface 71 of the protective sheet 70 includes the non-adhesive portions 73A and the adhesive portion 74. The overall adhesiveness of the protective sheet 70 can be adjusted by arranging the adhesive portion 74 and the non-adhesive portions 73A in a mixed pattern. More specifically, the area of the non-adhesive portions 73A may be adjusted beforehand so that the protective sheet 70 can be more easily removed from the first sheet member 40.

(1-10) In the present embodiment, the non-adhesive portions 73A of the protective sheet 70 are disposed at both end portions of the protective sheet 70 in the width direction. In the case where the non-adhesive portions 73A are disposed at the end portions of the protective sheet 70 in the width direction, when the protruding portion 56 is raised, the end portions of the second sheet member 50 and the first sheet member 40 at both ends in the width direction are raised from the end portions provided with the non-adhesive portions 73A. Accordingly, the opening between the two sheet members easily expands in the up-down direction into a three-dimensional shape. The more the opening expands three dimensionally, the more easily the oral device 10 can be inserted into the space between the first sheet member 40 and the second sheet member 50.

(1-11) In the present embodiment, the non-adhesive portions 73A of the facing surface 71 each have a substantially rectangular shape that extends in the longitudinal direction. When the non-adhesive portions 73A are shaped to extend in the longitudinal direction, the non-adhesive portions 73A can be easily disposed along both edges of the facing surface 71 in the width direction. Therefore, when the second sheet member 50 is raised upward, the joined portions of the first sheet member 40 and the second sheet member 50 at both ends in the width direction, which are not bonded to the protective sheet 70, can be easily raised. As a result, both ends of the substantially bag-shaped cover 20 can be easily raised so that the opening expands three-dimensionally.

(1-12) In the present embodiment, the maximum length W of the non-adhesive portions 73A in the width direction is about 15% of the maximum length of the facing surface 71 in the width direction. The protective sheet 70 may be manufactured by a so-called roll-to-roll process in which a rolled sheet having films arranged thereon at equal intervals, the films serving as the non-adhesive portions 73A, is rotated while being bonded to a rolled sheet having adhesiveness corresponding to that of the adhesive portion 74. However, this process requires a high equipment installation accuracy, and even a slight installation displacement leads to a dimensional error of the product. In the case where the maximum length W of the non-adhesive portions 73A of the protective sheet 70 in the width direction is about 15% of the length X of the facing surface 71 in the width direction at the first side, even when there are some dimensional errors in the width direction, there is a high possibility that the non-adhesive portions 73A can be disposed at both end portions of the facing surface 71 in the width direction.

(1-13) When the non-adhesive portions 73A are at both ends of the facing surface 71 of the protective sheet 70 in the width direction, there is a risk that the entirety of the protective sheet 70 will be removed from the first sheet member 40 starting from the non-adhesive portions 73A when the oral device 10 is inserted. In the present embodiment, the protective sheet 70 has a region where a portion of the adhesive portion 74 extends over the entire length of the facing surface 71 in the width direction. Since this portion of the adhesive portion 74 extends over the entire length of the facing surface 71 in the width direction, the risk of unexpected removal of the protective sheet 70 starting from the ends in the width direction can be reduced.

A second embodiment will now be described.

In the following description of the second embodiment, structures similar to those of the first embodiment are denoted by the same reference signs, and description thereof is omitted or simplified. The protective sheet 70 according to the first embodiment will be referred to as a first protective sheet 70. In addition, the facing surface 71 according to the first embodiment will be referred to as a first facing surface 71, and the adhesive portion 74 according to the first embodiment as a first adhesive portion 74.

Figure 5:
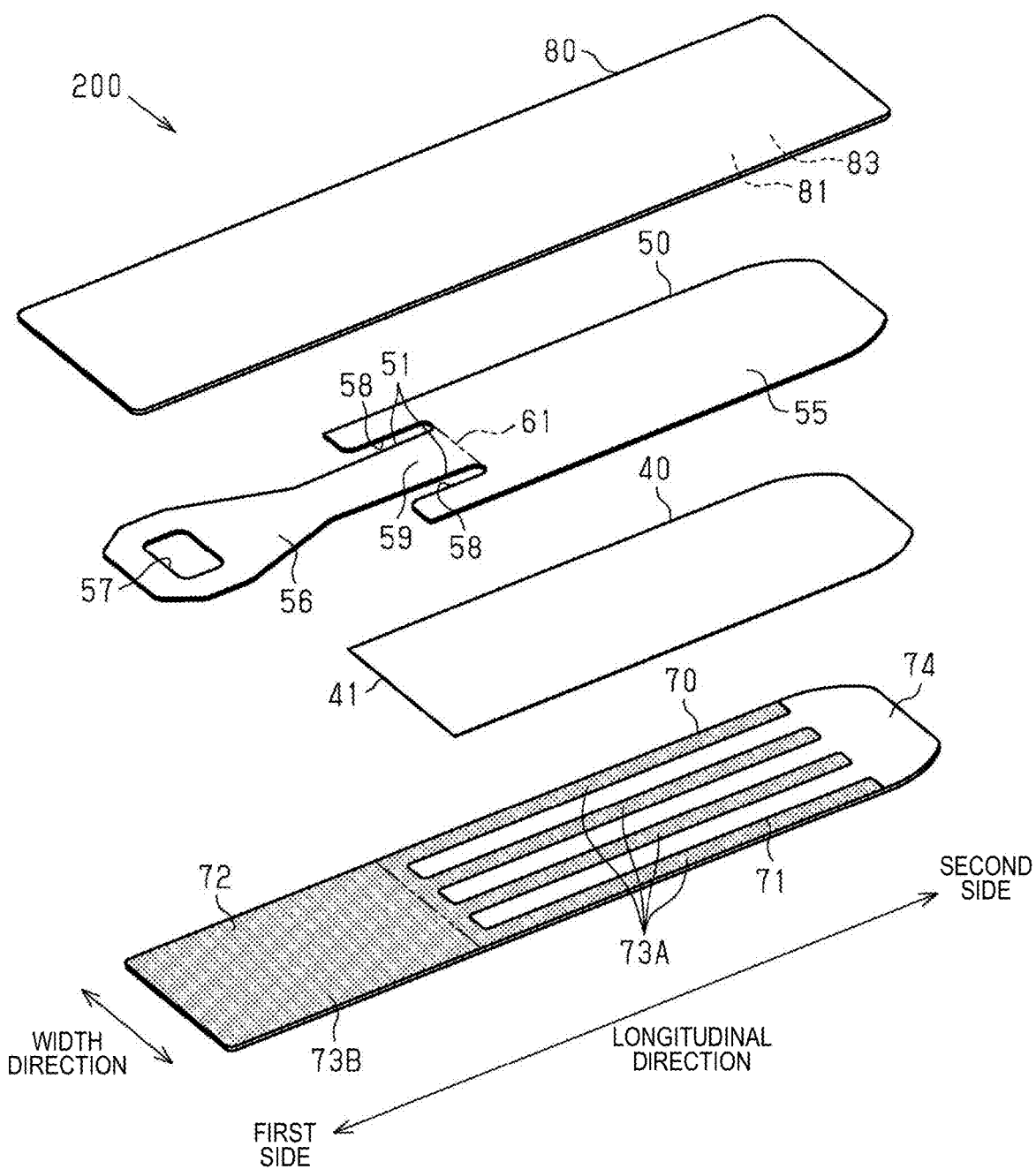
FIG. 5 is an exploded perspective view of a cover according to a second embodiment.
Figure 6:
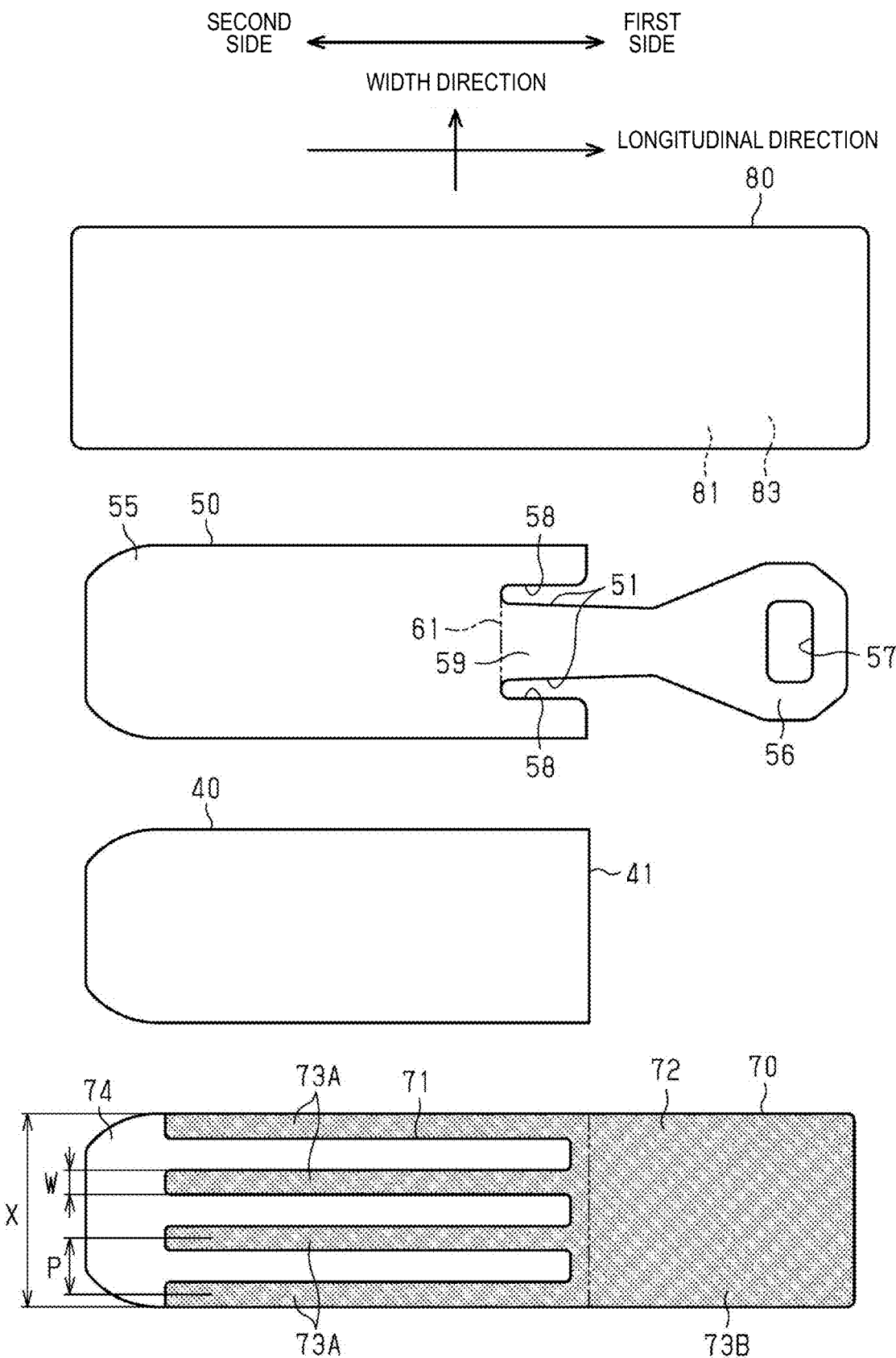
FIG. 6 is an exploded plan view of the cover according to the second embodiment.

As illustrated in FIGS. 5 and 6, a cover 200 according to the second embodiment includes a first sheet member 40, a second sheet member 50, and a first protective sheet 70. A second protective sheet 80, which is substantially sheet-shaped, is removably joined to the second sheet member 50 at a side opposite to the side at which the first sheet member 40 is provided. The second protective sheet 80 has a substantially rectangular shape that extends in the longitudinal direction. The dimension of the second protective sheet 80 in the longitudinal direction is slightly greater than the dimension of the first protective sheet 70 in the longitudinal direction. The dimension of the second protective sheet 80 in the width direction is slightly greater than the dimension of the first protective sheet 70 in the width direction. Thus, the overall dimensions of the second protective sheet 80 are greater than those of the first protective sheet 70.

The second protective sheet 80 has a second facing surface 81 that faces the second sheet member 50. The second facing surface 81 of the second protective sheet 80 includes a second adhesive portion 83 that is adhesive to another sheet member. In the present embodiment, the second adhesive portion 83 extends over the entire surface of the second protective sheet 80 that faces the second sheet member 50. In other words, the second adhesive portion 83 extends over the entire area of the second facing surface 81 including the outer edges of the second facing surface 81. The surface of the second protective sheet 80 at a side opposite to the second facing surface 81 is not adhesive to another sheet member.

The adhesiveness of the second adhesive portion 83 of the second protective sheet 80 is greater than the adhesiveness of the first adhesive portion 74 of the first protective sheet 70. The adhesiveness of the second adhesive portion 83 of the second protective sheet 80 is such that the second protective sheet 80 can be removed by the hand or fingers without, for example, tearing the sheet members. Thus, the second protective sheet 80 is removably joined to the second sheet member 50.

The material of the second protective sheet 80 is a synthetic resin, and may be, for example, a polyethylene terephthalate (PET). In the present embodiment, the second protective sheet 80 and the first protective sheet 70 are made of the same PET. The second protective sheet 80 is transparent. In other words, in this embodiment, the outer edges of the second sheet member 50 is visible through the second protective sheet 80. The thickness of the second protective sheet 80 may be about 80 micrometers to about 90 micrometers. Thus, the thickness of the second protective sheet 80 is greater than or equal to the thickness of the first protective sheet 70. Therefore, the flexural rigidity of the second protective sheet 80 is higher than or equal to the flexural rigidity of the first protective sheet 70. The cover 200 according to the second embodiment does not include the support member 60 according to the first embodiment.

The operation of the second embodiment will now be described.

To attach the cover 200 to the oral device 10, first, the cover 200 is positioned such that the first protective sheet 70 is at the lower side. Then, a portion of the second protective sheet 80 at the first side in the longitudinal direction is raised upward way from the first protective sheet 70. At this time, the protruding portion 56 of the second sheet member 50 is raised upward together with the second protective sheet 80 due to the adhesiveness of the second adhesive portion 83 of the second protective sheet 80.

After that, the raised end of the second protective sheet 80 at the first side in the longitudinal direction is moved toward the second side in the longitudinal direction, so that the lift-up portion 59 of the second sheet member 50 is lifted up. As a result, a space is created between the first sheet member 40 and the second sheet member 50.

Next, the oral device 10 is positioned such that the sensor 15 faces downward, and is inserted into the space created between the first sheet member 40 and the second sheet member 50. The oral device 10 is inserted until the distal end of the oral device 10 reaches the end of the first sheet member 40 and the second sheet member 50 at the second side in the longitudinal direction. When the oral device 10 is inserted in this manner, the shape of the space between the first sheet member 40 and the second sheet member 50 changes to a substantially columnar shape that corresponds to the shape of the oral device 10. Since the space between the first sheet member 40 and the second sheet member 50 extends in a substantially columnar shape, the ends of the second protective sheet 80 in the width direction are removed from the second sheet member 50.

When the oral device 10 is inserted into the mouth and used, the first protective sheet 70 is removed from the first sheet member 40, and the second protective sheet 80 is removed from the second sheet member 50. As a result, only the first sheet member 40 is disposed to face the sensor 15 of the oral device 10, so that the measurement in the mouth can be performed by the sensor 15. Although the measurement in the mouth can be performed with the second protective sheet 80 attached to the second sheet member 50, the second protective sheet 80 is preferably removed before the measurement to reduce discomfort experienced by the measurement subject when the second protective sheet 80 comes into contact with their mouth.

The effects of the second embodiment will now be described. In addition to the effects described above in (1-1) to (1-4) and (1-7) to (1-13) of the first embodiment, the cover 200 of the second embodiment provides the following effects.

(2-1) In the present embodiment, the second protective sheet 80 is removably joined to the second sheet member 50. The second protective sheet 80 is removed from the second sheet member 50 when the measurement is performed. Namely, the second sheet member 50 can be protected by the second protective sheet 80 until the measurement is performed, so that dust and the like do not easily adhere to the second sheet member 50 and that the second sheet member 50 can be maintained in a sanitary condition.

(2-2) In the present embodiment, the overall dimensions of the second protective sheet 80 are greater than those of the first protective sheet 70. Therefore, for example, by storing the cover 200 in a position such that the second protective sheet 80 faces outward, sheets of the cover 200 other than the second protective sheet 80 can be covered by the second protective sheet 80. Thus, when the cover 200 is in the stored state, adhesion of dust and the like to sheets other than the second protective sheet 80 can be prevented by the second protective sheet 80.

(2-3) In the present embodiment, the second protective sheet 80 has a flexural rigidity higher than or equal that of the first protective sheet 70. Accordingly, the flexural rigidity of the second protective sheet 80 is greater than the flexural rigidity of the second sheet member 50. Since the first sheet member 40 and the second sheet member 50 are sandwiched by the first protective sheet 70 and second protective sheet 80, which are appropriately rigid, these sheet members are not easily bent or wrinkled.

(2-4) In the present embodiment, the adhesiveness of the second adhesive portion 83 of the second protective sheet 80 is greater than the adhesiveness of the first adhesive portion 74 of the first protective sheet 70. Therefore, when the first protective sheet 70 and the second protective sheet 80 are pulled away from each other, the first protective sheet 70 is likely to be removed from the first sheet member 40. Therefore, the first protective sheet 70, which needs to be removed from the first sheet member 40 before the measurement of the mouth, can be prevented from being left attached.

(2-5) In the present embodiment, the second adhesive portion 83 extends over the entire area of the second facing surface 81 of the second protective sheet 80, so that the second facing surface 81 is adhesive over the entire area extending to the outer edges thereof. In addition, the dimensions of the second protective sheet 80 are greater than those of other sheets of the cover 200. Therefore, when an operator attaches the cover 200 to the oral device 10, the outer edges of the second protective sheet 80 easily come into contact with the hand of the operator. By touching the second adhesive portion 83 of the second protective sheet 80, the operator easily realizes that the second protective sheet 80 is left attached due to the adhesiveness of the second adhesive portion 83.

The above-described embodiments may be modified as described below. The above-described embodiments and modifications described below may be applied in combination as long as there is no technical contradiction.

The shape of the projecting portion 12 is not limited to a substantially triangular prism shape. The projecting portion 12 may have any shape as long as the projecting portion 12 is engageable with the through hole 57 in the second sheet member 50. Most preferably, the projecting portion 12 has a shape similar to that of the through hole 57 in the second sheet member 50 in top view.

The shape of the first sheet member 40 may be changed as appropriate. For example, the first sheet member 40 may have a substantially square shape or a substantially elliptical shape. The shape of the main portion 55 of the second sheet member 50 may be changed as appropriate in accordance with the shape of the first sheet member 40. In other words, the cover 20 including the first sheet member 40 and the second sheet member 50 that are joined together may have any shape as long as the cover 20 is substantially bag-shaped and can be opened at one end.

The flexural rigidity of the second sheet member 50 may be less than or equal to the flexural rigidity of the first sheet member 40 as long as the lift-up portion 59 of the second sheet member 50 can be raised without causing severe buckling when the protruding portion 56 of the second sheet member 50 is raised.

The position and shape of the lift-up portion 59 of the second sheet member 50 may be changed as appropriate. For example, the slits 58 in the second sheet member 50 may be omitted so that the lift-up portion 59 extends over the entire length of the main portion 55 in the width direction. In this case, the lift-up portion 59 can be raised away from the second sheet member 50 when both edges of the lift-up portion 59 in the width direction are not joined to the first sheet member 40, that is, when both edges of the second sheet member 50 in the width direction are not joined to the first sheet member 40 at the first side in the longitudinal direction. Alternatively, the lift-up portion 59 may be omitted if the protruding portion 56 can be raised so as to cause the first sheet member 40 and the second sheet member 50 to open appropriately.

The length of the protruding portion 56 along the outer edge 41 of the first sheet member 40 may be changed as appropriate. For example, the length of the protruding portion 56 may be greater than the length of the outer edge 41 of the first sheet member 40. In such a case, a central portion of the protruding portion 56 of the second sheet member 50 in the width direction may be raised by the hand or fingers to increase the area of the opening into which the oral device 10 is inserted.

The shape of the protruding portion 56 of the second sheet member 50 is not limited to that in the above-described embodiment. The shape of the second sheet member 50 may be changed as long as the second sheet member 50 protrudes from the outer edge of the first sheet member 40 at the first side in the longitudinal direction.

The shape of the through hole 57 that extends through the protruding portion 56 at the first side in the longitudinal direction may be changed as appropriate. The through hole 57 may have, for example, a substantially circular shape as long as the projecting portion 12 of the oral device 10 can be inserted therethrough. Alternatively, the through hole 57 in the protruding portion 56 may be omitted. In such a case, the cover 20 may be prevented from moving in the direction toward the distal end of the oral device 10 by, for example, placing adhesion tape or the like on a portion of the protruding portion 56 that faces the oral device 10 or holding the cover 20 by the hand or fingers.

Figure 7:
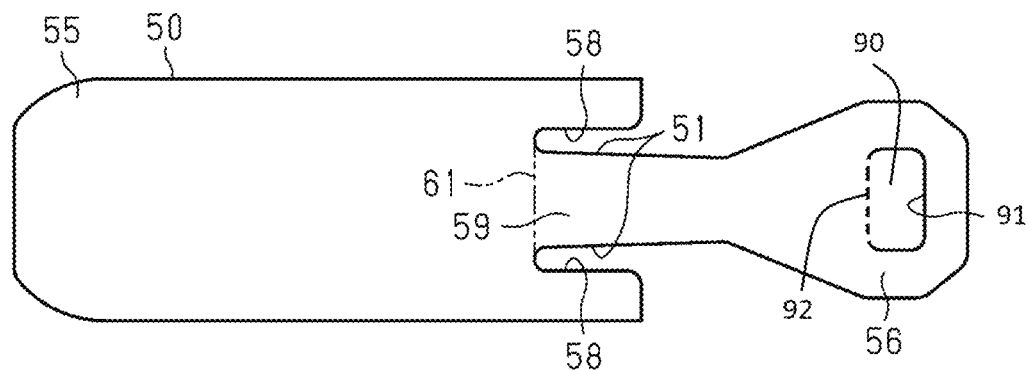
FIG. 7 is a plan view of an alternative configuration of the second sheet.

In an alternate embodiment shown in FIG. 7, the through hole 57 can be omitted and a flap 90 can be formed by having a cut or score line 91 and a fold line 92. With such a modification, the flap 90 will separate from the 50 along the cut or score line 90 so as to engage the projecting portion 12 of the oral device 10. Such a configuration will prevent any hollowed-out sheet piece of the through hole 57 from accidentally entering the subject's mouth during measurement. Because the flap 90 stays connected to the cover 20 at the fold line 92, pieces are prevented from breaking off and accidentally being swallowed by the subject.

In the first embodiment, the position at which the support member 60 is joined to the second sheet member 50 may be changed as appropriate. Preferably, the support member 60 is disposed in a central region of the second sheet member 50 in the width direction so that the support member 60 serves as a reinforcement for raising the second sheet member 50 without causing buckling. The shape of the support member 60 may also be changed as appropriate to, for example, a substantially triangular shape or a substantially elliptical shape.

In the first embodiment, the cover 20 does not necessarily include the support member 60 when the flexural rigidity of the second sheet member 50 is sufficiently high.

The adhesive portion 74 may be formed to extend over a portion or the entirety of the non-facing surface 72 of the protective sheet 70. When the area of the non-facing surface 72 is small or when the adhesive portion 74 has a low adhesiveness, the protruding portion 56 that is in contact with the non-facing surface 72 can be easily removed from the non-facing surface 72.

The adhesive portion 74 may be formed to extend over the entire region of the facing surface 71 of the protective sheet 70. In such a case, the adhesiveness of the adhesive portion 74 of the facing surface 71 is preferably such that the protective sheet 70 does not fall off the first sheet member 40 but can be easily removed from the first sheet member 40 by the hand or fingers when intended.

Figure 8:
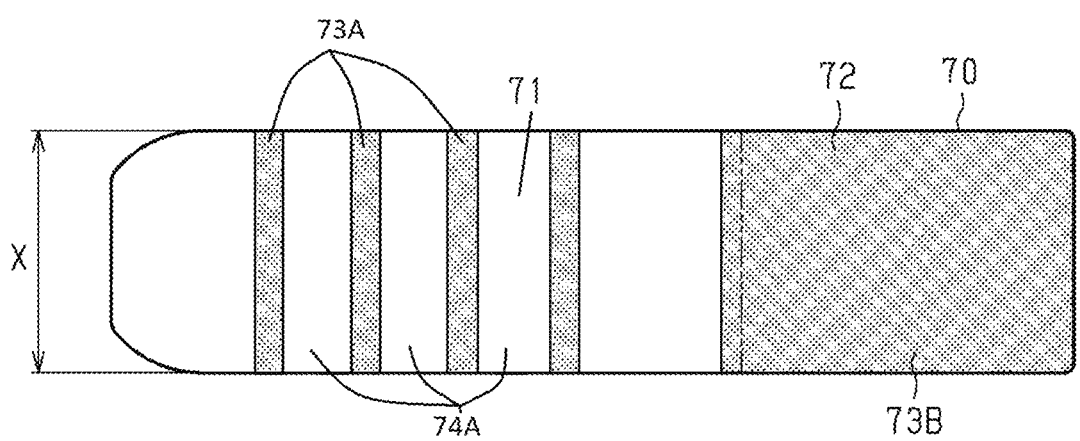
FIG. 8 is a plan view of an alternative arrangement of the adhesive portion of the protective sheet.

In addition, while the first and second embodiments have the adhesive portion 74 extend along an end portion of the facing surface 71 at the second side in the longitudinal direction over the entire length of the facing surface 71 in the width direction, the adhesive portion does not require this configuration. Because the non-adhesive portions 73A are disposed at both ends in the width direction in the first and second embodiments, the first sheet member 40 may turn upward when the oral device 10 is inserted. Also, depending on the process used, it may be difficult to accurately form the non-adhesive portions 73A evenly on the left and right sides of the protective sheet 70. If the left and right sides are not even, the cover 20 may become twisted when attached to the oral device 10. Thus, and as shown in FIG. 8, the facing surface 71 of the protective sheet 70 can include a plurality of adhesive portions 74A separated by intervening non-adhesive portions 73A, where each extend across the entire length X of the facing surface 71 in the width direction of the protective sheet 70. As a result, the adhesive portions 74A extend along the entire width of the facing surface 71 in the width direction and the non-adhesive portions 73A are evenly disposed on the left and right, and the cover does is prevented from twisting and wrinkling when inserting the oral device 10. Further, since the adhesive portions 74A extend along the entire width of the facing surface 71 in the width direction, the adhesive portions 74A extend outside of the first sheet member. This prevents the first sheet member from being turned up, which allows the oral device 10 to be easily inserted.

The shape of the protective sheet 70 may be changed as appropriate. The protective sheet 70 is preferably shaped to cover a portion of the first sheet member 40 that faces the sensor 15 during the measurement. The protective sheet 70 may be omitted when the cover 20 is stacked on another cover 20 so that the first sheet member 40, which comes into contact with the measurement object during the measurement, is covered until the measurement is performed.

The non-adhesive portions 73A and the non-adhesive portion 73B may be replaced by weak adhesive portions (i.e., second adhesive portions) that are adhesive. The adhesiveness of the weak adhesive portions is not limited as long as the adhesiveness is sufficiently less than that of the adhesive portion 74 (i.e., first adhesive portion) and the protective sheet 70 can be removed from the first sheet member 40 as easily as in the case where the non-adhesive portions 73A and the non-adhesive portion 73B are provided.

The non-adhesive portions 73A of the facing surface 71 may be disposed only at one side of the facing surface 71 in the width direction. Also, the non-adhesive portions 73A are not necessarily disposed at the edges of the facing surface 71 in the width direction.

The non-adhesive portions 73A of the facing surface 71 do not necessarily have a substantially rectangular shape, and may instead have, for example, a substantially square shape or a substantially perfectly circular shape. However, a shape that extends in the longitudinal direction, such as a substantially elliptical shape or a substantially wavy shape, is preferred.

The number of non-adhesive portions 73A of the facing surface 71 may be changed as appropriate. For example, two may be provided at both ends of the facing surface 71 in the width direction, or only one may be provided at one end of the facing surface 71 in the width direction. Alternatively, more than four may be provided. In addition, the non-adhesive portions 73A are not necessarily arranged at equal intervals in the width direction of the facing surface 71, and may instead be arranged at different intervals.

The maximum length W of the non-adhesive portions 73A of the facing surface 71 in the width direction may be changed as appropriate. For example, the maximum length W may be less than about 10% of the length X of the facing surface 71 in the width direction at the first side. Also, the pitch P of the non-adhesive portions 73A in the width direction of the facing surface 71 may be an integer ratio of the length X of the facing surface 71 in the width direction at the first side. In such a case, preferably, the protective sheet 70 is manufactured with care to reduce manufacturing errors, and the non-adhesive portions 73A are disposed at both end portions of the facing surface 71 in the width direction.

The non-adhesive portions 73A may extend over the entire length of the facing surface 71 from the first side to the second side in the longitudinal direction so that the adhesive portion 74 does not extend over the entire length of the facing surface 71 in the width direction. When the portions of the adhesive portion 74 that are arranged alternately with the non-adhesive portions 73A in the width direction have sufficient adhesiveness, the protective sheet 70 can be prevented from falling off the first sheet member 40.

The materials of the protective sheet 70, the first sheet member 40, the second sheet member 50, and the support member 60 are not limited to those in the above-described embodiments. For example, the material of the protective sheet 70 may be a synthetic resin such as polypropylene, polyethylene, nylon, polyvinyl chloride, or polyimide. Alternatively, the material may be paper or nonwoven fabric. The protective sheet 70, the first sheet member 40, the second sheet member 50, and the support member 60 may be made of different materials.

The first sheet member 40 and the second sheet member 50 may have a plurality of openings therebetween. For example, the first sheet member 40 and the second sheet member 50 may be partially joined together at the second side in the longitudinal direction and at both end portions in the width direction, and may have a plurality of openings between the joined portions as long as the first sheet member 40 and the second sheet member 50 form a substantially bag-like shape overall.

The structures of the first sheet member 40 and the second sheet member 50 of the cover 20 are not limited to those in the above-described embodiments as long as the first sheet member 40 and the second sheet member 50 face each other. For example, a single sheet may be folded in half such that portions of the sheet that face each other with the folding line at the boundary serve as the first sheet member 40 and the second sheet member 50. In this case, a substantially bag-shaped cover 20 can be obtained by joining the portions of the half-folded sheet along the edges at two of the sides other than the folded side.

The structure of the oral device 10 is not limited to that in the above-described embodiments. The oral device 10 may be any device that is used in the mouth. Examples of such an oral device include a moisture checker, an occlusal force sensor, a tongue pressure sensor, an ultrasonic echo device, an electromagnetic wave therapeutic device, a thermometer, and various dental tools.

In the second embodiment, the shape of the second protective sheet 80 is not limited to that in the second embodiment. The second protective sheet 80 may have, for example, a substantially elliptical shape as long as the second protective sheet 80 is larger than the first protective sheet 70.

In the second embodiment, the second adhesive portion 83 of the second protective sheet 80 may be provided on a portion of the second facing surface 81. More specifically, the second adhesive portion 83 is not necessarily provided on the outer edges of the second facing surface 81.

In the second embodiment, the adhesiveness of the second adhesive portion 83 of the second protective sheet 80 may be less than or equal to the adhesiveness of the first adhesive portion 74 of the first protective sheet 70. The adhesiveness of the second adhesive portion 83 of the second protective sheet 80 is preferably such that the second protective sheet 80 and the second sheet member 50 are raised together in a joined state when the oral device 10 is inserted into the cover 200.

In the second embodiment, the thickness of the second protective sheet 80 is not limited to that in the second embodiment. When, for example, the material of the second protective sheet 80 has a flexural rigidity higher than that of the material of the first protective sheet 70, the second protective sheet 80 may have a thickness less than that of the first protective sheet 70.

In the second embodiment, the second protective sheet 80 may have a flexural rigidity less than that of the first protective sheet 70. The flexural rigidity of the second protective sheet 80 is preferably such that the second protective sheet 80 serves as a reinforcement for the second sheet member 50 when the second sheet member 50 is raised.

The cover 200 according to the second embodiment may include the support member 60 according to the first embodiment. In such a case, the support member 60 is positioned between the second sheet member 50 and the second protective sheet 80.

In the second embodiment, the color of the second protective sheet 80 may be different from that of the first protective sheet 70. Here, different colors are colors that are visually distinguishable based on the hue, saturation, and brightness. When the first protective sheet 70 and the second protective sheet 80 are in different colors, the upper and lower surfaces of the cover 200 can be easily distinguished from each other. This facilitates correct attachment of the cover 200 to the oral device 10.

In the second embodiment, the second protective sheet 80 is not necessarily transparent. When the second protective sheet 80 is transparent, the manner in which the oral device 10 is inserted into the space between the second sheet member 50 and the first sheet member 40 can be easily checked, and the cover 200 can be easily attached. The second protective sheet 80 may be translucent, instead of being completely transparent, such that the manner in which the oral device 10 is inserted into the space between the second sheet member 50 and the first sheet member 40 can be checked.

While preferred embodiments of the invention have been described above, it is to be understood that variations and modifications will be apparent to those skilled in the art without departing from the scope and spirit of the invention. The scope of the invention, therefore, is to be determined solely by the following claims.

What is claimed is:

1. A cover for covering at least a portion of an oral device that is used in a mouth, the cover comprising:
    a first sheet member made of a first resin;
    a second sheet member made of a second resin and facing the first sheet member, wherein when a first direction is a direction along a surface of the first sheet member and a second direction is a direction along the surface of the first sheet member and orthogonal to the first direction, the first sheet member and the second sheet member are joined to each other in a bag shape so as to define an opening at a first side in the first direction; and
    a protruding portion that protrudes from the second sheet member and past an outer edge of the first sheet member at the opening in the first direction,
    wherein the second sheet member has slits therein, the slits being positioned on opposed sides of the protruding portion in the second direction, the slits extending from a part of the opening defined by the second sheet member toward a second side in the first direction opposite the first side such that the part of the opening defined by the second sheet member and including the slits is a non-linear edge of the second sheet member.

2. The cover according to claim 1, wherein a flexural rigidity of the second sheet member is higher than a flexural rigidity of the first sheet member.

3. The cover according to claim 1, wherein the second sheet member includes a lift-up portion that adjoins the protruding portion to the second sheet member, and the lift-up portion is not joined to the first sheet member over an entirety of the lift-up portion including opposed edges thereof in the second direction.

4. A cover for covering at least a portion of an oral device that is used in a mouth, the cover comprising:
    a first sheet member made of a first resin;
    a second sheet member made of a second resin and facing the first sheet member, wherein when a first direction is a direction along a surface of the first sheet member and a second direction is a direction along the surface of the first sheet member and orthogonal to the first direction, the first sheet member and the second sheet member are joined to each other in a bag shape so as to define an opening at a first side in the first direction;

a protruding portion that protrudes from the second sheet member and past an outer edge of the first sheet member at the opening in the first direction; and a protective sheet removably joined to the first sheet member at a side thereof opposite to a side facing the second sheet member, wherein the protective sheet has a facing surface that faces the first sheet member, the facing surface including a first adhesive portion and a second adhesive portion having adhesiveness less than that of the first adhesive portion, and wherein the second adhesive portion is disposed at each of opposed sides of the facing surface of the protective sheet in the second direction.

5. The cover according to claim 4, wherein the second adhesive portion comprises a plurality of second adhesive portions that extend in the first direction and that are arranged with equal intervals therebetween in the second direction.

6. The cover according to claim 4, wherein a portion of the first adhesive portion extends over an entire width of the facing surface in the second direction.

7. The cover according to claim 4, wherein the protective sheet is a first protective sheet, and the cover further comprises:

a second protective sheet removably joined to the second sheet member at a side thereof opposite to a side facing the first sheet member.

8. The cover according to claim 7, wherein a dimension of the second protective sheet in the first direction is greater than a dimension of the first protective sheet in the first direction, and a dimension of the second protective sheet in the second direction is greater than a dimension of the first protective sheet in the second direction.

9. The cover according to claim 8, wherein a flexural rigidity of the second protective sheet is higher than or equal to a flexural rigidity of the first protective sheet.

10. The cover according to claim 7, wherein the facing surface of the first protective sheet is a first facing surface, the second protective sheet has a second facing surface that faces the second sheet member, the second facing surface has a third adhesive portion having adhesiveness, and the adhesiveness of the third adhesive portion is greater than the adhesiveness of the first adhesive portion.

11. The cover according to claim 10, wherein the third adhesive portion is at least at an outer edge of the second facing surface.

12. The cover according to claim 1, further comprising a sheet-shaped support member joined to the second sheet member at a side thereof opposite to a side facing the first sheet member.

13. The cover according to claim 3, further comprising a sheet-shaped support member joined to the second sheet member at a side thereof opposite to a side facing the first sheet member.

14. The cover according to claim 13, wherein the support member extends across an edge of the lift-up portion at the second side in the first direction.

15. A cover for covering at least a portion of an oral device that is used in a mouth, the cover comprising:

a first sheet member made of a first resin;

a second sheet member made of a second resin and facing the first sheet member, wherein when a first direction is a direction along a surface of the first sheet member and a second direction is a direction along the surface of the first sheet member and orthogonal to the first direction, the first sheet member and the second sheet member are joined to each other in a bag shape so as to define an opening at a first side in the first direction;

a protruding portion that protrudes from the second sheet member and past an outer edge of the first sheet member at the opening in the first direction; and a protective sheet removably joined to the first sheet member at a side thereof opposite to a side facing the second sheet member, wherein the protective sheet has a facing surface that faces the first sheet member, the facing surface including a first adhesive portion and a second adhesive portion having adhesiveness less than that of the first adhesive portion, and wherein the second adhesive portion extends from a first side to a second side of the facing surface of the protective sheet in the second direction.

16. The cover according to claim 15, wherein there are a plurality of second adhesive portions, and the plurality of second adhesive portions are disposed at intervals with respect to each other in the second direction.

17. The cover according to claim 1, wherein the protruding portion includes flap at the first side in the longitudinal direction, the flap being defined by a cut or score line.

* * * * *